US009105071B2

(12) United States Patent
Fletcher et al.

(10) Patent No.: US 9,105,071 B2
(45) Date of Patent: Aug. 11, 2015

(54) SYSTEM MANAGEMENT OF CLINICAL PROCEDURES SCHEDULING BASED ON ENVIRONMENTAL THRESHOLDS

(71) Applicant: International Business Machines Corporation, Armonk, NY (US)

(72) Inventors: James C. Fletcher, Apex, NC (US); Derek W. Botti, Holly Springs, NC (US)

(73) Assignee: International Business Machines Corporation, Armonk, NY (US)

( * ) Notice: Subject to any disclaimer, the term of this patent is extended or adjusted under 35 U.S.C. 154(b) by 279 days.

(21) Appl. No.: 13/630,361

(22) Filed: Sep. 28, 2012

(65) Prior Publication Data

US 2014/0095182 A1   Apr. 3, 2014

(51) Int. Cl.
*G06Q 50/00* (2012.01)
*G06Q 50/22* (2012.01)
*G06Q 10/06* (2012.01)

(52) U.S. Cl.
CPC .......... *G06Q 50/22* (2013.01); *G06Q 10/06311* (2013.01)

(58) Field of Classification Search
None
See application file for complete search history.

(56) References Cited

U.S. PATENT DOCUMENTS

| | | | |
|---|---|---|---|
| 8,799,011 B2 * | 8/2014 | Wilson et al. ................. | 705/2 |
| 2008/0146892 A1 | 6/2008 | LeBoeuf et al. | |
| 2008/0281152 A1 | 11/2008 | Lau et al. | |
| 2009/0089092 A1 | 4/2009 | Johnson et al. | |
| 2011/0112854 A1 * | 5/2011 | Koch et al. ................. | 705/2 |
| 2011/0125539 A1 | 5/2011 | Bollapragada et al. | |

OTHER PUBLICATIONS

Arnold, Scott; "Johnson Controls Launches Healthcare Environment Optimization"; Heating/Piping/Air Conditioning HPAC Engineering; Jul. 19, 2011; Printed: Jun. 8, 2012; <http://hpac.com/news/johnson-controls-healthcare-environment-optimization/>.

Glass, Don; "Why Operating Rooms Are So Cold"; A Moment of Science—Indiana . . . ; Posted: Sep. 27, 2003; Printed Sep. 27, 2012; <http://www.indianapublicmedia.org/amamentofscience/why-operating-rooms-are-so-cold/>.

(Continued)

*Primary Examiner* — Michelle L Le
(74) *Attorney, Agent, or Firm* — Arnold B. Bangali; Jeffrey LaBaw

(57) ABSTRACT

An approach for scheduling clinical procedures based on defined environmental thresholds of medical units in healthcare facilities. In one embodiment, a computer system monitors environmental conditions of the medical unit in which clinical procedures will be performed utilizing a measurement system that includes an environmental device for monitoring the environmental conditions. The computer system further receives a schedule of the clinical procedures of the medical unit. The computer system further identifies environmental thresholds for the medical unit to be used for comparison against the environmental conditions of the medical unit. The computer system further compares environmental conditions to the environmental threshold to determine if the environmental thresholds are violated. In another embodiment, the computer system modifies the schedule of clinical procedures of the medical unit responsive to the determination.

8 Claims, 3 Drawing Sheets

(56) References Cited

OTHER PUBLICATIONS

Groner, F. Gabriel, et al.; "Special Feature: Requirements Analysis in Clinical Research Information Processing a Case Study"; IP.com Prior Art Database; IPCOM000131450D; Original Publication: Sep. 1, 1979; IEEE Computer vol. 12; No. 9; pp. 101-108; Electronic Publication: Nov. 11, 2005; Copyright: 1979 Institute of Electrical and Electronics Engineers, Inc.; <http://www.ip.com.pubvieew/IPCOM000131450D>.

IBM; "Monitoring Solution to Automatically Determine When a Resource is out of Norm"; IP.com Prior Art Database; IPCOM000029730D; Original Publication: Jul. 9, 2004; Electronic Publication: Jul. 9, 2004; <http://www.ip.com/pubview/IPCOM000029730D>.

Millard, Mike; "Saving energy—and money—in surgery"; Healthcare IT News; Printed Jun. 8, 2012; <http://www.healthcareitnews.com/news/saving-energy---and-money---surgery>.

"Helping patients heal. Helping hospitals prosper"; Healthcare Environment Optimization; Johnson Controls; Copyright 2012 Johnson Controls, Inc.

\* cited by examiner

SYSTEM MANAGEMENT OF CLINICAL PROCEDURES SCHEDULING BASED ON ENVIRONMENTAL THRESHOLDS

FIELD OF THE INVENTION

The present invention relates generally to scheduling systems in healthcare institutions, and more particularly to management and monitoring of clinical procedural scheduling based on environmental enterprise thresholds defined for medical units of one or more healthcare institutions, such as hospitals or clinics.

BACKGROUND

Healthcare institutions, including for example, medical hospitals or clinics, are regularly tasked with providing efficient clinical or medical services to patients, including, individuals, families or communities, with curative, preventive, rehabilitative, or palliative care, while utilizing limited hospital staff or medical equipment. Further, management of hospital resources, including, for example, atmospheric or environmental resources, is also important in providing efficient clinical services to patients of the hospitals. Moreover, certain hospitals are equipped with building management systems to monitor and provide appropriate environmental resource measurements of various medical units within the hospitals.

Building management systems can also regulate heating, ventilation and air conditioning (HVAC) within certain buildings, or within enclosed space, including, for example, medical units of hospitals. However, certain medical units of hospitals are required to operate under specific environmental or atmospheric parameters or conditions in order for clinical procedures to be executed or performed in the medical units in accordance with domestic or international healthcare environmental mandates.

SUMMARY

The present invention includes a method, system and computer program product for management and monitoring of clinical procedural scheduling based on environmental enterprise thresholds defined for medical units of one or more healthcare institutions.

In one embodiment, a method is provided for scheduling clinical procedures within a computer system based on environmental thresholds. The computer system monitors environmental conditions of a medical unit in which clinical procedures will be performed utilizing a measurement system that includes an environmental device for monitoring the environmental conditions. The computer system also receives a schedule of clinical procedures of the medical unit. The computer system further identifies environmental thresholds for the medical unit to be used for comparison against the environmental conditions of the medical unit. In at least one embodiment, the computer system compares environmental conditions to the environmental threshold to determine if the environmental thresholds are violated. Responsive to the determination, the computer system modifies the schedule of clinical procedures of the medical unit.

BRIEF DESCRIPTION OF THE SEVERAL VIEWS OF THE DRAWINGS

Novel characteristics of the invention are set forth in the appended claims. The invention itself, as well as, preferred mode of use, further objectives, and advantages thereof, will be best understood by reference to the following detailed description of the invention when read in conjunction with the accompanying figures, wherein like reference numerals indicate like components, and:

DETAILED DESCRIPTION

Figure 1:
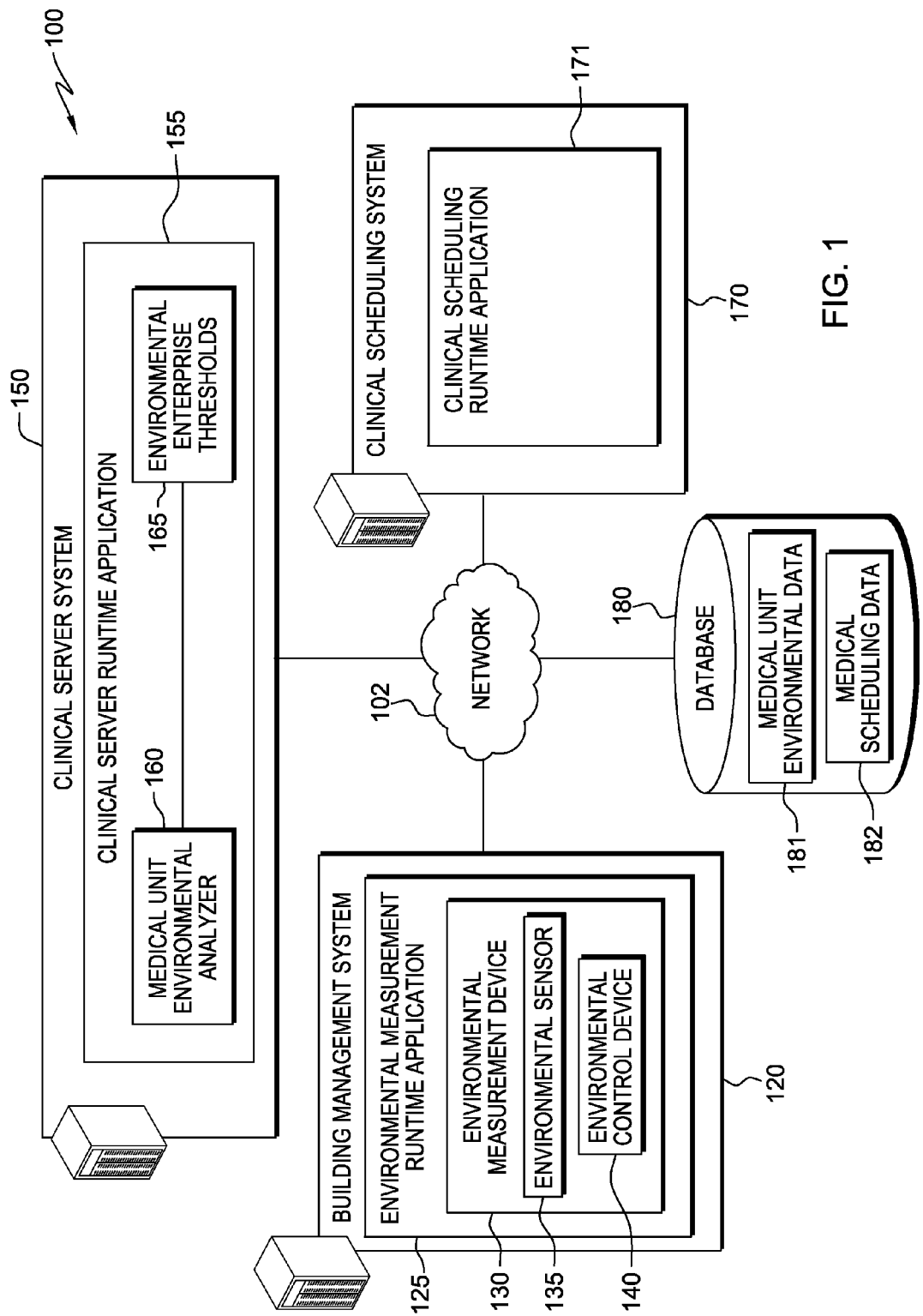
FIG. 1 is a functional block diagram of a hospital scheduling management system in accordance with embodiments of the present invention.

Embodiments of the present invention comprise functionalities for monitoring environmental conditions based on defined environmental thresholds of medical units of hospitals, medical clinics, or other healthcare institutions in which clinical procedures are executed or performed. In particular, medical units, including, for example, cardiac catheterization laboratories, endoscopy laboratories, and surgical laboratories are required to comply with environmental requirements, including, Facilities Guidelines Institute environment requirements, Joint Commission environment requirements, or other environmentally required operations or conditions, specifically defined for the medical units of the hospital. Furthermore, anesthesiologists, nurses or other medical personnel in hospitals or medical clinics are required to schedule clinical procedures in medical units or surgical suites based on required environmental or atmospheric conditions of the medical units or surgical suites. However, ongoing scheduling of clinical procedures in medical units can be a difficult task to accomplishment in a demanding medical atmosphere.

Embodiments to the present invention include one or more circuits or subassemblies of circuits, as well as, methods of operation that are executed to monitor environmental conditions for medical units based on defined environmental thresholds for the medical units. Embodiments of the present invention also include management of clinical procedural scheduling of clinical scheduling systems of the medical units based on comparison of the monitored environmental conditions and the defined environmental enterprise thresholds, in accordance with at least one embodiment.

In particular, a clinical server system monitors environmental conditions or parameters of the medical units by monitoring measurements of the environmental conditions provided by a measurement device of the medical unit. The measurement device is a building management system or an environmental management system. In another embodiment, the clinical server system is further adapted to dynamically receive a schedule of clinical procedures stored in a database of a hospital scheduling management system. In addition, the clinical server system identifies environmental enterprise thresholds defined in an environmental enterprise threshold unit of the clinical server system. Furthermore, a medical unit environmental analyzer of the clinical server system compares environmental conditions measured by the measurement device against the environmental enterprise thresholds by querying the state of operation of the building management system to determine if the environmental enterprise thresholds are violated by the measured environmental conditions of the medical unit. In one preferred embodiment, responsive to the comparison, the clinical server system triggers a clinical scheduling system of the medical unit to transfer or alter scheduled clinical procedures of the clinical scheduling system to another medical unit of the hospital, as described in more detail below, in accordance with embodiments of the present invention.

Further embodiments of the present invention will now be described in conjunction with the Figures. Referring to FIG. 1, hospital scheduling management system 100 for managing medical scheduling of clinical procedures based on environmental enterprise thresholds defined for medical units of hospitals or clinics, in accordance with embodiments of the present invention is shown.

Hospital scheduling management system 100 includes building management system 120, network 102, clinical scheduling system 170, clinical server system 150 and database 180. In the depicted embodiment, building management system 120 operates to communicate over network 102 with clinical server system 150 and clinical scheduling system 170 to facilitate monitoring of environmental conditions of the medical units based on the defined environmental enterprise thresholds, and managing scheduling of clinical procedures based on the monitored environmental conditions and the defined environmental enterprise thresholds of the medical unit, in accordance with one embodiment of the present invention.

Building management system 120 is a server computing system such as a management server, a web server, or any other electronic device or computing system capable of receiving and sending data, according to one embodiment of the present invention. In one embodiment, the building management system 120 represents a "cloud" of computers interconnected by one or more networks, wherein the building management system 120 is a primary server for a computing system utilizing clustered computers when accessed through a virtual computing environment. Building management system 120 can also be a laptop, tablet, or notebook personal computer (PC), a desktop computer, a mainframe or mini computer, a personal digital assistant (PDA), or a smart phone such as a Blackberry® (Blackberry is a registered trademark of Research in Motion Limited (RIM) Inc., in the United States, other countries, or both) or iPhone® (iPhone is a registered trademark of Apple Inc., in the United States, other countries, or both), respectively.

Building management system 120 monitors environmental conditions or environmental parameters of buildings or closed spaces. In one embodiment of the present invention, the enclosed space or building is a medical unit, including, for example, cardiac cauterization laboratories, endoscopy laboratories, and surgical laboratories of hospitals or clinics that are monitored by building management system 120 based on defined environmental enterprise threshold of medical units.

In one embodiment, building management system 120 provides central environmental monitoring capabilities within the enclosed space or building by regulating operational components with the enclosed space, including, for example, heating, ventilation and air conditioning (HVAC) of the enclosed space. Building management system 120 includes sensors operating within building management system 120 to monitor the environmental conditions or parameters of the medical units. For example, the environmental conditions include temperature, energy, water or pressure conditions that can be measured by the sensors within the medical units. Moreover, building management system 120 utilizes humidity and carbon dioxide content measurements of the medical units to determine and adjust rate of air consumption within the medical units. Building management system 120 includes environmental measurement runtime application 125. Environmental measurement runtime application 125 performs all necessary functions to record environmental conditions of medical units measured by building management system 120.

Network 102 includes one or more networks of any kind that provides communication links between various devices and computers connected together within hospital scheduling management system 100. Network 102 can also include connections, such as wired communication links, wireless communication links, or fiber optic cables. In addition, network 102 can be implemented as a number of different types of networks, including, for example, a local area network (LAN), wide area network (WAN) or a packet switched telephone network (PSTN), or some other networked system. Network 102 includes the Internet representing a worldwide collection of networks. The term "Internet" as used according to embodiments of the present invention refers to a network or networks that uses certain protocols, such as the TCP/IP protocol, and possibly other protocols such as the hypertext transfer protocol (HTTP) for hypertext markup language (HTML) documents that make up the world wide Web (the web). At the heart of the Internet is a backbone of high-speed data communication lines between major nodes or host computers, consisting of thousands of commercial, government, educational nodes.

Clinical server system 150 is, for example, a server computer system such as a management server, a web server, or any other electronic device or computing system capable of receiving and sending data. Moreover, clinical server system 150 also represents a "cloud" of computers interconnected by one or more networks, where clinical server system 150 is a primary server for a computing system utilizing clustered computers when accessed through network 102, in accordance with embodiments of the present invention.

Clinical server system 150 includes clinical server runtime application 155. In one embodiment, clinical server runtime application 155 performs all necessary functions to compare environmental conditions or parameters stored in database 180 against environmental enterprise thresholds. Clinical server system 150 further performs alteration or modification of clinical procedures of clinical scheduling system 170 based on the comparison, as described below, in accordance with embodiments of the present invention.

Clinical scheduling system 170 includes a server computing system such as a management server, a web server, or any other electronic device or computing system capable of receiving and sending data. The server computing system represents a "cloud" of computers interconnected by one or more networks, wherein the clinical scheduling system 170 is the primary server for a computing system utilizing clustered computers when accessed through network 102, in accordance with embodiments of the present invention. Clinical scheduling system 170 can also be for example, a laptop, tablet, or notebook personal computer (PC), a desktop computer, a mainframe or mini computer, a personal digital assistant (PDA), or a smart phone such as a Blackberry® or iPhone® in accordance with embodiments of the present invention.

In one embodiment, clinical scheduling system 170 manages scheduling of medical units or surgical suites including, for example, cauterization laboratories, radiotherapy laboratories, or patient operating theaters, based on defined environment or atmospheric thresholds of the medical unit. In one embodiment, clinical scheduling system 170 manages scheduling of clinical procedures for the medical units. Clinical scheduling system 170 coordinates availability of hospital medical resources or medical units in which clinical procedures can be performed.

Operations performed by clinical scheduling system 170 include, for example, medical unit scheduling management, medical personnel scheduling management, or hospital schedule administrative management. For example, clinical scheduling system 170 coordinates availability of medical units for the clinical procedures, availability of medical devices in one or more medical units of the hospital, availability of medical personnel to perform the clinical procedures in the medical unit, including, for example, anesthesiologists, surgical nurses or other medical personnel, in accordance with embodiments of the present invention.

In one preferred embodiment, clinical scheduling system 170 manages scheduling of clinical procedures of medical units based on monitored environmental conditions of the medical units. In one embodiment, clinical scheduling system 170 stores clinical procedural schedules of the medical units in database 180.

Clinical scheduling system 170 includes clinical scheduling runtime application 171. Clinical scheduling runtime application 171 operates to manage scheduling of the medical units based on defined environment of clinical server system 150, in accordance with embodiments of the present invention. In one embodiment, clinical scheduling runtime application 171 is a software system or plug-in that is executed within clinical scheduling system 170 to expose the state of program operation of clinical scheduling system 170.

For example, clinical scheduling runtime application 171 provides integrated collaboration functionality between clinical server system 150, clinical scheduling system 170 and building management system 120 to monitor environmental conditions measured by building management system 120 of medical units, to compare the monitored environmental conditions against defined environmental enterprise thresholds in the clinical server system 150, and to update schedules of clinical procedures of the medical units based on the comparison. In one embodiment, clinical scheduling runtime application 171 provides one or more system functionalities of a typical scheduling system, including, for example, email, calendaring, contacts management, instant messaging, voice and video conferencing, online meetings, discussions, forums, and user directories. Clinical scheduling runtime application 171 can be, for example, IBM® Lotus Notes® (IBM and Lotus Notes are registered trademarks of International Business Machines Corporation in the United States, other countries of both), that is executed within clinical scheduling system 170 to expose the state of program operation of clinical scheduling system 170.

Database 180 is any type of storage device, storage server, storage area network, redundant array of independent discs (RAID), cloud storage device, or any type of data storage. In one preferred embodiment, database 180 is a relational database management system (RDBMS). RDBMS is a database that stores information from documents in a table, and also defines relationships among the information in the table. Database 180 includes medical unit environmental data 181 and medical scheduling data 182. Medical unit environmental data 181 includes information pertaining to environmental conditions of medical units of building management system 120. Medical unit scheduling data 182 includes information pertaining to schedules of clinical procedures of medical units.

In the depicted embodiment, environmental measurement runtime application 125 records measurements monitored by building management system 120 of one or more medical units. In one embodiment, environmental measurement runtime application 125 is be a web browser, a standalone web page data management application, a data management software application, or part of a service that operates to monitor management of environmental conditions or parameters stored in database 180 against environmental enterprise thresholds. Examples of web browsers can include Internet Explorer® (Internet Explorer is a trademark of Microsoft Inc., in the United States, other countries, or both), Firefox® (Firefox is a trademark of Mozilla Corporation, in the United States, other countries, or both), Safari® (Safari is a trademark of Apple, Inc. in the United States, other countries, or both) and Google Chrome™ (Google Chrome is a trademark of Google, Inc. in the United States, other countries, or both), respectively.

Environmental measurement runtime application 125 includes environmental measurement device 130. Environmental measurement device 130 detects and measures environmental parameters within the enclosed space or housing, including the surgical or patient care units, or other enclosed units of hospitals or medical clinics of building management system. In one embodiment, environmental measurement device 130 is operational with environmental sensor 135 and environmental control device 140 Environmental sensor 135 detects environmental parameters including temperature, humidity, oxygen, carbon dioxide, carbon monoxide, or airflow rate within the surgical or patient care units of the hospitals or medical clinics, in accordance with embodiments of the present invention. Environmental control device 140 is an automatic control device that controls environmental parameters within the surgical or patient care units. Environmental control device 140 is a fan, blower, or louver of a heating, ventilation, and air conditioning (HVAC) system. Further, environmental control device 140 is also an automated feature of the surgical or patient care units of the hospital that blocks passage of air or light into the surgical or patient care unit. Environmental control device 140 also monitors temperature setting of a furnace or air conditioning units within the HVAC system of building management system 120.

In one embodiment, environmental control device 140 is configured to adjust and redirect environmental controls to meet specifically defined environmental thresholds of building management system 120 based on detected environmental parameters by environmental sensor 135. For example, environmental control device 140 can adjust carbon dioxide in the surgical or patient units based on the environmental parameters, or also activate blowers, fans, louvers, or temperature controls of a furnace or air cooling element of the surgical or patient units of building management system. In this manner, the adjusted or redirected environmental controls are utilized by clinical scheduling system 170 to update or modify medical schedules defined for specific surgical or operating units based on the defined environmental threshold as discussed below, in accordance with embodiments of the present invention.

Once the environmental parameters are measured by environmental measurement device 130, environmental measurement runtime application 125 stores the measured environmental parameters in medical unit environmental data 181 of database 180. In particular, environmental measurement runtime application 125 stores the measured environmental parameters in medical unit environmental data 181 periodically, randomly, and/or using event-based storing of environmental data of medical units in database 180. In one preferred embodiment, clinical server system 150 performs functions to manage the stored environmental parameters. Specifically, clinical server system 150 compares the stored environmental parameters against defined environmental thresholds of clinical server runtime application 155. Further, clinical server system 150 alters or modify schedules of clinical procedures of clinical scheduling system based on the comparison.

In one embodiment, clinical server runtime application 155 supports monitoring of the environmental parameters of medical units stored in medical unit environmental data 181. In particular, clinical server runtime application 155 operates to manage the state of hardware and software operations of building management system 120 during execution of clinical server runtime application 155. Further, clinical server runtime application 155 contains implementations of basic low level commands, and may also implement higher level commands of program applications operating within environmental measurement runtime application 125 of building management system 120 to monitor the state of the stored environmental parameters, in accordance with embodiments of the present invention.

In another embodiment, clinical server runtime application 155 provides integrated collaborative functionality between building management system 120 and clinical scheduling system 170 based on defined environment thresholds in clinical server runtime application 155. In one preferred embodiment, modification of clinical schedules by clinical scheduling system 170 is based on the managed collaborative functionality between building management system 120 and environmental enterprise thresholds of clinical server runtime application 155, as described in further details below, in accordance with embodiments of the invention. Clinical server runtime application 155 includes medical unit environmental analyzer 160 and environmental enterprise thresholds 165.

Medical unit environmental analyzer 160 compares the stored environmental parameters in medical unit environmental data 181 against environmental enterprise thresholds stored in environmental enterprise thresholds 165. In one embodiment, environmental enterprise thresholds 165 includes defined environmental thresholds for medical units based on clinical procedures that are performed in the medical unit. For example, medical units, including cardiac cauterization laboratories, endoscopy laboratories, and surgical laboratories have distinct environmental requirements for temperature, pressure, and humidity to be in a specific threshold for execution of clinical procedures. In one embodiment, medical unit environmental analyzer 160 queries the state of measurement of environmental parameters stored in medical unit environmental data 181 of database 180 by environmental measurement runtime application 125, to determine whether the defined environmental enterprise thresholds for one or more medical units within the hospital are violated based on the stored environmental parameters.

In one preferred embodiment, responsive to the comparison, the medical unit environmental analyzer 160 triggers the clinical scheduling system 170 of the medical unit to transfer scheduled clinical procedures to another medical unit based on determination of whether the other medical unit violates the defined environmental enterprise thresholds. In one embodiment, if it is determined that the other medical unit does not violate the environmental enterprise thresholds, the clinical procedure will be transferred to the other medical unit. In one embodiment, the clinical procedure is transferred based on time, date, or designated location of the clinical procedure of the medical unit.

In another embodiment, if the environment thresholds are violated, clinical server system 150 also triggers environmental measurement runtime application 125 of the building management system 120 to alter or modify environment control device 140 of the monitored medical unit to accommodate environmental conditions required by the environment enterprises thresholds, in accordance with embodiments of the present invention.

Figure 2:
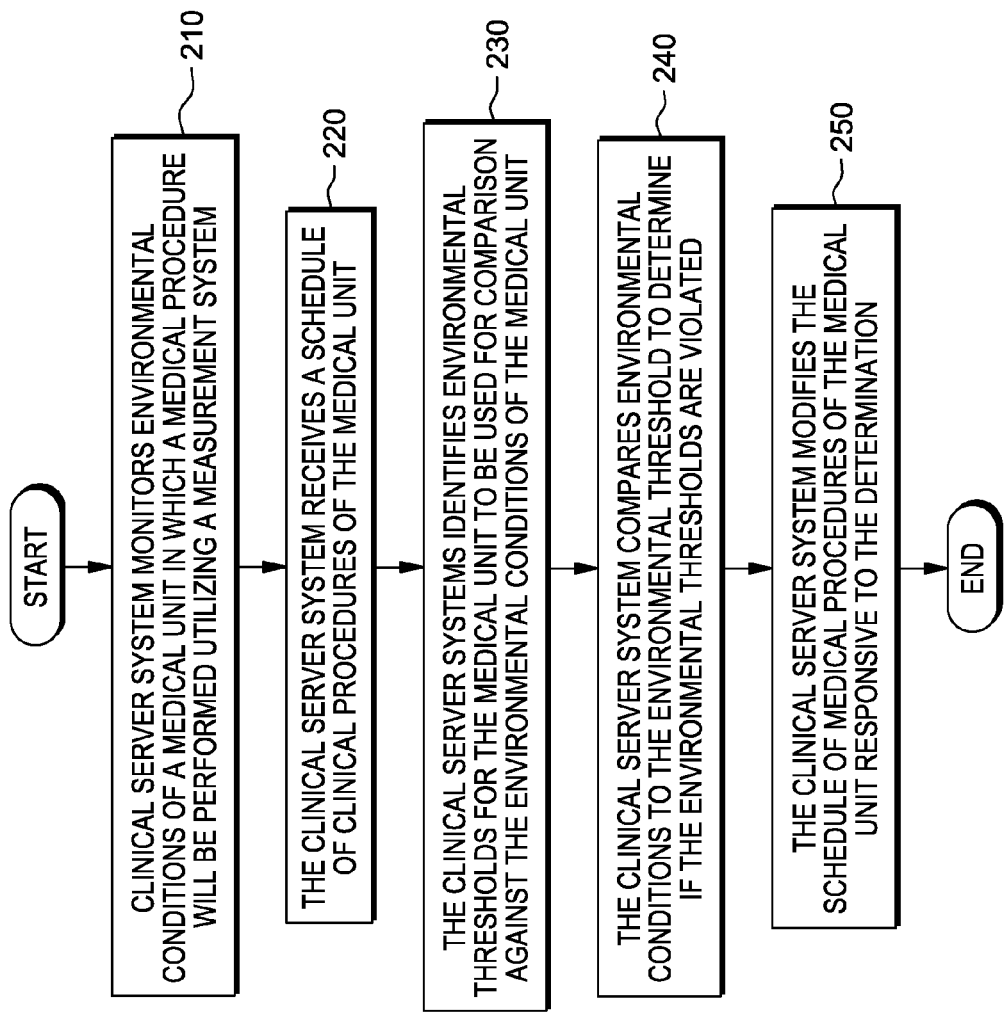
FIG. 2 is a flowchart depicting steps performed by a clinical server runtime application of a clinical server system in accordance with embodiments of the present invention.

FIG. 2 is a flowchart depicting steps performed by clinical server runtime application 155 of clinical server system 150 of FIG. 1, according to one embodiment of the present invention. In step 210, clinical server runtime application 155 monitors environmental conditions of a medical unit in which a clinical procedure is performed utilizing a building management system 120. In one embodiment, building management system 120 stores the measured environmental conditions in medical unit environmental data 181 of database 180.

In step 220, clinical server runtime application 155 receives a schedule of clinical procedures from medical scheduling data 182 of database 180 and analyzes the state of the scheduled clinical procedures of clinical scheduling system 170 based on environment enterprise thresholds of clinical server program 155. In particular, medical unit environmental analyzer 160 queries the state of measurement of environmental parameters stored in medical unit environmental data 181 of database 180 by environmental measurement runtime application 125.

In step 230, clinical server runtime application 155 identifies environmental thresholds for the medical unit based on environmental thresholds of environmental enterprise thresholds 165. In step 240, clinical server runtime application 155 compares the environmental conditions to the environmental threshold to determine if the environmental thresholds are violated. In step 250, clinical server runtime application 155 triggers clinical scheduling system application 171 of clinical scheduling system 170 to modify scheduled clinical procedures or create a new schedule for clinical procedure in one or more medical units.

Figure 3:
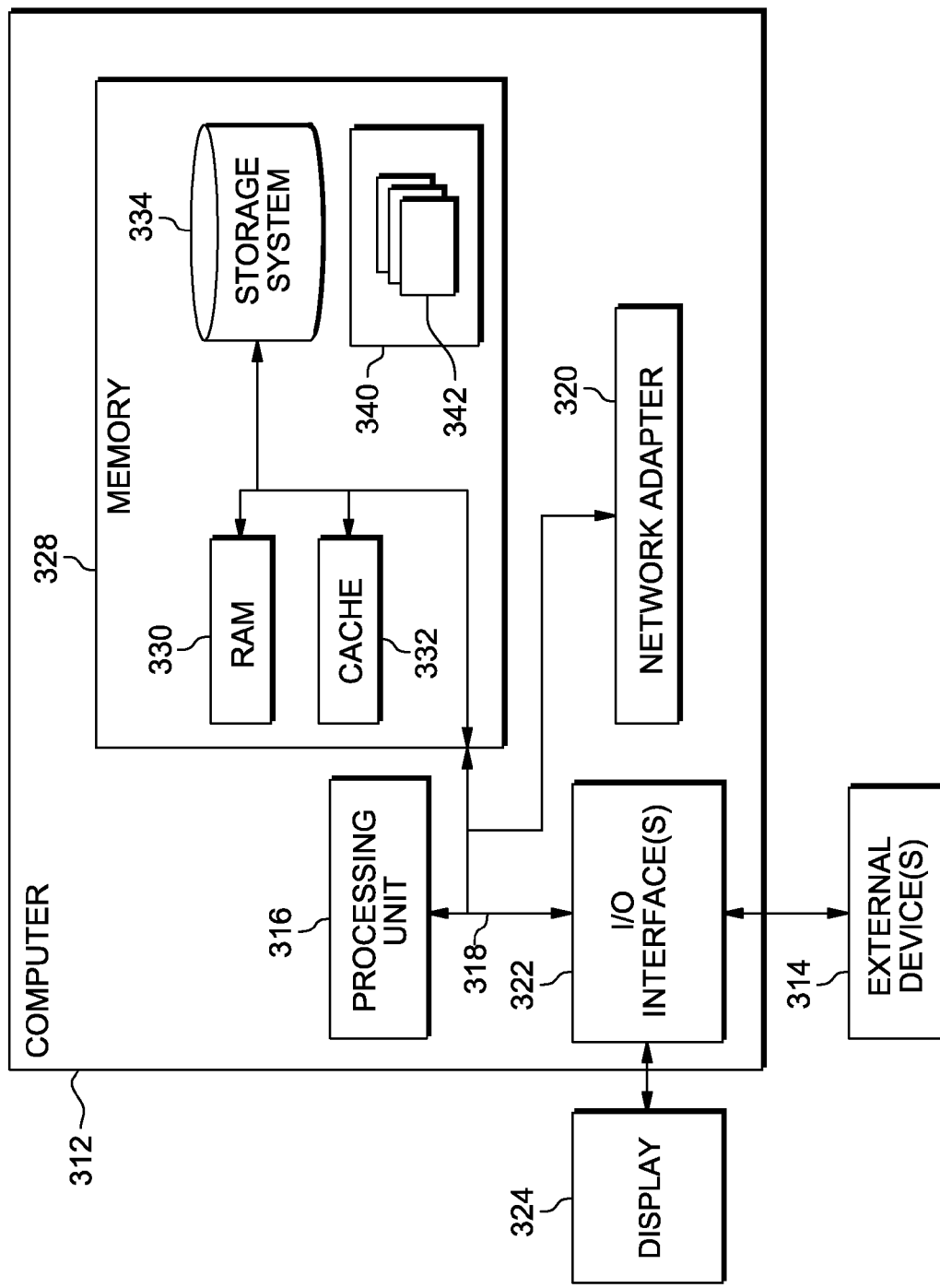
FIG. 3 illustrates a block diagram of components of a computer system in accordance with embodiments of the present invention.

FIG. 3 is a functional block diagram of a computer system, in accordance with an embodiment of the present invention. Computer system 300 is only one example of a suitable computer system and is not intended to suggest any limitation as to the scope of use or functionality of embodiments of the invention described herein. Regardless, computer system 300 is capable of being implemented and/or performing any of the functionality set forth hereinabove. In computer system 300 there is computer 312, which is operational with numerous other general purpose or special purpose computing system environments or configurations. Examples of well-known computing systems, environments, and/or configurations that may be suitable for use with computer 312 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. Each one of building management system 120, clinical scheduling system 170, clinical server system 150 and database 180 can include or can be implemented as an instance of computer 312.

Computer 312 may be described in the general context of computer system executable instructions, such as program modules, being executed by a computer system. Generally, program modules may include routines, programs, objects, components, logic, data structures, and so on that perform particular tasks or implement particular abstract data types. Computer 312 may be practiced in distributed cloud computing environments where tasks are performed by remote processing devices that are linked through a communications network. In a distributed cloud computing environment, program modules may be located in both local and remote computer system storage media including memory storage devices.

As further shown in FIG. 3, computer 312 is shown in the form of a general-purpose computing device. The components of computer 312 may include, but are not limited to, one or more processors or processing units 316, memory 328, and bus 318 that couples various system components including memory 328 to processing unit 316.

Bus 318 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer 312 typically includes a variety of computer system readable media. Such media may be any available media that is accessible by computer 312, and includes both volatile and non-volatile media, and removable and non-removable media.

Memory 328 includes computer system readable media in the form of volatile memory, such as random access memory (RAM) 330 and/or cache 332. Computer 312 may further include other removable/non-removable, volatile/non-volatile computer system storage media. By way of example only, storage system 334 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 318 by one or more data media interfaces. As will be further depicted and described below, memory 328 may include at least one program product having a set (e.g., at least one) of program modules that are configured to carry out the functions of embodiments of the invention.

Environmental measurement runtime application 125, clinical scheduling runtime application 171 and clinical server runtime application 155 may be stored in memory 328 by way of example, and not limitation, as well as an operating system, one or more application programs, other program modules, and program data. Each of the operating system, one or more application programs, other program modules, and program data or some combination thereof, may include an implementation of a networking environment. Program modules 342 generally carry out the functions and/or methodologies of embodiments of the invention as described herein. Each one of environmental measurement runtime application 125, clinical scheduling runtime application 171 and clinical server runtime application 155 are implemented as or are an instance of program 340.

Computer 312 may also communicate with one or more external devices 314 such as a keyboard, a pointing device, etc., as well as display 324; one or more devices that enable a user to interact with computer 312; and/or any devices (e.g., network card, modem, etc.) that enable computer 312 to communicate with one or more other computing devices. Such communication occurs via Input/Output (I/O) interfaces 322. Still yet, computer 312 communicates with one or more networks such as a local area network (LAN), a general wide area network (WAN), and/or a public network (e.g., the Internet) via network adapter 320. As depicted, network adapter 320 communicates with the other components of computer 312 via bus 318. It should be understood that although not shown, other hardware and/or software components could be used in conjunction with computer 312. Examples, include, but are not limited to: microcode, device drivers, redundant processing units, external disk drive arrays, RAID systems, tape drives, and data archival storage systems, etc.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustrations are implemented by special purpose hardware-based systems that perform the specified functions or acts, or combinations of special purpose hardware and computer instructions.

As will be appreciated by one skilled in the art, embodiments of the present invention may be embodied as a system, method or computer program product. Accordingly, embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the present invention may take the form of a computer program product embodied in one or more computer-readable medium(s) having computer-readable program code embodied thereon.

In addition, any combination of one or more computer-readable medium(s) may be utilized. The computer-readable medium may be a computer-readable signal medium or a computer-readable storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that contains, or stores a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that communicates, propagate, or transport a program for use by or in connection with an instruction execution system, apparatus, or device. The term "computer readable tangible storage device" does not encompass a signal propagation medium such as a copper cable, optical fiber, or wireless transmission medium.

Program code embodied on a computer-readable medium may be transmitted using any appropriate medium, including but not limited to wireless, wireline, optical fiber cable, RF, etc., or any suitable combination of the foregoing. Computer program code for carrying out operations for embodiments of the present invention may be written in any combination of one or more programming languages, including an object oriented programming language such as Java, Smalltalk, C++ or the like, conventional procedural programming languages such as the "C" programming language, a hardware description language such as Verilog, or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Based on the foregoing a method, system and computer program product for management and monitoring of clinical procedural scheduling based on environmental enterprise thresholds defined for medical units of one or more healthcare institutions has been described. However, numerous modifications and substitutions can be made without deviating from the scope of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the Figures. Therefore, the present invention has been disclosed by way of example and not limitation.

What is claimed is:

1. A method for scheduling clinical procedures within a computer system, within a bi-directional computing environment, based on environmental thresholds, the method comprising the steps of:

a clinical server system, monitoring environmental conditions of a medical unit in which a clinical procedure will be performed utilizing a unit measurement system that includes an environmental device for monitoring the environmental conditions, wherein the unit measurement system comprises environmental control and, wherein the environmental control is temperature control device of unit management system;

the clinical server system, receiving, via a clinical scheduling system, a schedule of clinical procedures of the medical unit, wherein the scheduling system manages time, date or location of clinical procedures within one or more medical units of a facility;

the clinical server system identifying environmental thresholds defined in an environmental enterprise threshold unit of the clinical server system, for the medical units, via, an environmental sensor of an environmental measurement device, wherein identified environmental threshold is used for comparison against defined environmental threshold conditions for the medical unit;

the clinical server system comparing via a medical unit environmental analyzer, environmental conditions against the environmental threshold to determine if the environmental thresholds are violated, wherein the medical unit environmental analyzer queries the state of operations of the unit management system to determine if the environmental thresholds are violated by measured and monitored environmental conditions of the medical units; and the clinical server system modifying the schedule of clinical procedures of the medical unit based on the compared environmental threshold, responsive to the determination, wherein the scheduled clinical procedures are transferred to another medical unit, or conditions of the medical units are adjusted to meet the identified environmental thresholds of the medical units, if the environmental thresholds are violated of the medical unit are violated.

2. The method according to claim 1 further comprising the step of:
determining if environmental conditions of the other medical unit violate the environmental threshold; and
transferring the scheduled clinical procedures to the other medical unit if the environmental conditions of the other medical unit do not violate the environmental threshold.

3. The method according to claim 1, wherein an environment analyzer of the computing system queries the state of operation of the building management system to determine if environmental thresholds are violated by measured environmental conditions of the medical unit based on environmental parameters stored in a repository.

4. A computer system for scheduling clinical procedures, within a bi-directional computing environment, based on environmental thresholds, the computer system comprising:
one or more processors, one or more computer-readable memories, one or more computer-readable tangible storage devices and program instructions which are stored on at least one of the one or more storage devices for execution by at least one of the one or more processors via at least one of the one or more memories, the program instructions comprising:
program instructions to monitor environmental conditions of a medical unit in which clinical procedures will be performed utilizing a measurement system that includes an environmental device for monitoring the environmental conditions, wherein the unit measurement system comprises environmental control and, wherein the environmental control is temperature control device of unit management system;
program instructions to receive via a clinical scheduling system, a schedule of clinical procedures of the medical unit, wherein the scheduling system manages time, date or location of clinical procedures within one or more medical units of a facility;

program instructions to identify environmental thresholds defined in an environmental enterprise threshold unit of the clinical server system, for the medical units, via, an environmental sensor of an environmental measurement device, wherein identified environmental threshold is used for comparison against defined environmental threshold conditions for the medical unit;

program instructions to compare via a medical unit environmental analyzer, environmental conditions against the environmental threshold to determine if the environmental thresholds are violated, wherein the medical unit environmental analyzer queries the state of operations of the unit management system to determine if the environmental thresholds are violated by measured and monitored environmental conditions of the medical units; and program instructions to modify the schedule of clinical procedures of the medical unit based on the compared environmental threshold, responsive to the determination, wherein the scheduled clinical procedures are transferred to another medical unit, or conditions of the medical units are adjusted to meet the identified environmental thresholds of the medical units, if the environmental thresholds are violated of the medical unit are violated.

5. The computer system according to claim 4, wherein program instructions to modify the schedule of clinical procedures of the medical unit further comprise:

program instructions to trigger a scheduling system of a healthcare facility to transfer the scheduled clinical procedures to another medical unit.

6. The computer system according to claim 4, wherein an environment analyzer of the computing system queries the state of operation of the building management system to determine if environmental thresholds are violated by measured environmental conditions of the medical unit.

7. A program product for scheduling clinical procedures based on environmental thresholds, the program product comprising:

one or more computer-readable tangible storage devices and program instructions stored on at least one of the one or more storage devices, the program instructions comprising:

program instructions to monitor environmental conditions of a medical unit in which clinical procedures will be performed utilizing a measurement system that includes an environmental device for monitoring the environmental conditions, wherein the unit measurement system comprises environmental control and, wherein the environmental control is temperature control device of unit management system;

program instructions to receive via a clinical scheduling system, a schedule of clinical procedures of the medical unit, wherein the scheduling system manages time, date or location of clinical procedures within one or more medical units of a facility;

program instructions to identify environmental thresholds defined in an environmental enterprise threshold unit of the clinical server system, for the medical units, via, an environmental sensor of an environmental measurement device, wherein identified environmental threshold is used for comparison against defined environmental threshold conditions for the medical unit;

program instructions to compare via a medical unit environmental analyzer, environmental conditions against the environmental threshold to determine if the environmental thresholds are violated, wherein the medical unit environmental analyzer queries the state of operations of the unit management system to determine if the environmental thresholds are violated by measured and monitored environmental conditions of the medical units; and program instructions to modify the schedule of clinical procedures of the medical unit based on the compared environmental threshold, responsive to the determination, wherein the scheduled clinical procedures are transferred to another medical unit, or conditions of the medical units are adjusted to meet the identified environmental thresholds of the medical units, if the environmental thresholds are violated of the medical unit are violated.

8. The program product according to claim 7 further comprising:

program instructions to determine if environmental conditions of the other medical units violates the environmental thresholds; and program instructions to transfer the scheduled clinical procedures to the other medical units if it does not violate the environmental thresholds.

* * * * *